United States Patent [19]

Bright

[11] Patent Number: 4,590,290

[45] Date of Patent: May 20, 1986

[54] PROCESS FOR THE PREPARATION OF 6-METHOXY-1-NAPHTHOIC ACID, METHYL ESTERS

[75] Inventor: John H. Bright, Norwalk, Conn.

[73] Assignee: American Cyanamid Company, Stamford, Conn.

[21] Appl. No.: 708,138

[22] Filed: Mar. 4, 1985

[51] Int. Cl.$^4$ .............................................. C07C 69/76
[52] U.S. Cl. ....................................................... 560/56
[58] Field of Search ............................................ 560/56

[56] References Cited

U.S. PATENT DOCUMENTS 4,328,356  5/1982  Giordano et al. ...................... 560/56

FOREIGN PATENT DOCUMENTS 7145841  9/1982  Japan ...................................... 560/56
9098037  6/1984  Japan ...................................... 560/56

Primary Examiner—Paul J. Killos
Attorney, Agent, or Firm—Gordon L. Hart

[57] ABSTRACT

Yield of methyl-6-methoxy-1-naphthalene carboxylate is increased by reacting dimethyl sulfate with 6-hydroxy-1-naphthoic acid in organic solvent having flash point greater than 10° C. and that is insoluble in water, in presence of mixed carbonates and hydroxides of alkali metal.

8 Claims, No Drawings 9.4 g (0.15 mole) potassium hydroxide as a 60% aqueous solution. Then dimethyl sulfate, 25.4 g (0.20 mole), is added dropwise over 15 minutes at 50°–52° C. The mixture is stirred at 50°–52° C. for one hour. Then more potassium hydroxide, 9.4 g (0.15) as a 60 wt. % aqueous solution, is added over 10 minutes at 52°–65° C. Dimethyl sulfate, 25.4 g (0.20 mole), is added over 15 minutes at 60°–65° C. The mixture is further heated for one-half hour at 70°–75° C. TLC indicates no remaining 6-hydroxy-1-naphthalenecarboxylic acid, but methyl 6-methoxy-1-naphthalenecarboxylate and methyl 6-hydroxy-1-naphthalenecarboxylate. Heating for another hour at 70° C. brings no change to the TLC.

Additional potassium hydroxide, 2.0 g (0.03 mole) as 50 wt. % aqueous solution, and dimethyl sulfate, 8.8 g (0.07 mole), are added at 70° C. After another hour of heating at 70° C., no change is seen by TLC. Another 2.0 (0.03 mole) of potassium hydroxide is added followed by one-half hour of heating at 70° C.; no change in the TLC is observed.

To isolate product, water, 200 mL, is added to the above solution cooled to room temperature. After stirring for 20 minutes, the organic layer is separated and the volatile solvent exhaustively stripped at 65° C. under a water aspirator vacuum in a rotary vacuum evaporator. To the residue is added 300 mL of heptane. Heating to 60° C. with stirring results in a solution. Upon cooling to room temperature the heptane solution is separated from a residue of insoluble tar and is treated with 2 g of decolorizing carbon with stirring and heating to 60° C. for one-half hour. Filtration of the slurry through filter paper, prepared with 5 g, heptane-wet, filter aid gives a brown solution. The solution is exhaustively stripped using a rotary vacuum evaporator as above to give 18.0 g (assay 74.7%) of methyl 6-methoxy-1-naphthalenecarboxylate yield, 37%.

EXAMPLE 4

6-Hydroxy-1-naphthalenecarboxylic acid, 31.7 g (0.17 mole), granular potassium carbonate, 24.5 g (0.175 mole), and dimethyl sulfate, 42.5 g (0.34 mole), are added to 500 mL of butyl acetate and heated with stirring at 50°–55° C. for two hours. Then additional potassium carbonate, 24.5 g (0.175 mole), is added and the mixture is heated with stirring at 80°–93° C. for three hours.

To isolate product, volatiles including the butyl acetate solvent are stripped off at 60° C. under vacuum in a rotary vacuum evaporator. To the residue is added 300 mL of heptane and 150 mL of water. The mixture is stirred at 60° C. for three-fourths hour. The organic solution is separated. The organic solution is washed by stirring with 75 mL of fresh water for three-fourths hour at room temperature. The two layers are filtered to remove insolubles and separate the organic layer. The organic solution is treated with 2 g of decolorizing carbon and then is stirred and heated to 60° C. for one-half hour. Filtration of the slurry through filter paper prepared with 5 g of heptane-wet filter aid gives a brown solution. The solution is exhaustively stripped using a rotary vacuum evaporator as above to give 14.0 g (assay 43.7%) 17% yield of methyl 6-methoxy-1-naphthalenecarboxylate.

EXAMPLE 5

6-Hydroxy-1-naphthalenecarboxylic acid, 31.7 g (0.17 mole), is dissolved into 450 mL of butyl acetate with stirring and heating to 75° C. Powdered potassium carbonate, 24.5 g (0.175 mole), is added all at once. Dimethyl sulfate, 25.0 g (0.20 mole), is added dropwise over five minutes. The mixture is stirred at 85°–90° C. for one and one-half hours. Additionally, powdered potassium carbonate, 24.5 g (0.175 mole), and dimethyl sulfate, 25.0 g (0.20 mole), are charged at 85° C. and the mixture stirred and heated for two hours at 85°–90° C. The mixture TLC shows significant methyl 6-hydroxy-1-naphthalenecarboxylate present. After adding more dimethyl sulfate, 8.5 g (0.07 mole), and heating for two hours at 85°–90° C., no change is observed on the mixture TLC. After adding more powdered potassium carbonate, 4.9 g (0.03 mole), and heating for one hour at 85°–90° C., no change is observed on the mixture TLC. After adding still more dimethyl sulfate, 8.5 g (0.07 mole), and heating for one hour at 85° C., no change is observed on the mixture TLC. After adding still more dimethyl sulfate, 8.5 g (0.07 mole), and heating for two hours at 85° C., no change is observed on the mixture TLC. Finally, after adding still more powdered potassium carbonate, 65 g (0.46 mole), and heating to 118° C. for one-half hour, no change is observed on the mixture TLC.

To isolate product the mixture is cooled to room temperature and solids are filtered off. The filter cake is washed with 50 mL of fresh butyl acetate and combined with the filtrate. The butyl acetate solution is washed by stirring for 15–30 minutes with 200 mL water. After separation, the organic layer is stripped of volatiles at 65° C. under vacuum in a rotary vacuum evaporator. The resulting oil is cooled to room temperature and treated with 400 mL of heptane at 60° C. with stirring for one hour. After cooling to 30°–40°, the heptane solution is decanted from residual insoluble tar and heated with 2 g of decolorizing charcoal for 15–30 minutes at 60°–70°. Filtration of the slurry through filter paper prepared with 5 g of heptane-wet filter aid gives a brown solution, which is exhaustively stripped using a rotary vacuum evaporator as above to give 25.5 g (assay 41.0%) or 29% yield of methyl 6-methoxy-1-naphthalenecarboxylate.

THIN LAYER CHROMATOGRAPHY METHOD (TLC)

One mL of reaction solution is filtered through a Millipore Millex 0.5 micron filter. The filtered sample is diluted one to six with ethyl acetate. Two-five λ of diluted sample is spotted on Analtech Silica Gel GF glass plates and developed with one to one volumes of ethyl acetate/heptane. The resulting spots are observed under UV light (254 μm) and compared with known concentrations of authentic standards.

ASSAY BY HIGH PERFORMANCE LIQUID CHROMATOGRAPHY (HPLC)

Isolated methyl 6-methoxy-1-naphthalenecarboxylate samples dissolved in methanol were assayed by reversed phase HPLC. A mobile phase gradient of dilute aqueous phosphoric acid and methanol at constant tetrahydrofuran concentration was used through a 5 μm particle size $C_{18}$ column.

PROCESS FOR THE PREPARATION OF 6-METHOXY-1-NAPHTHOIC ACID, METHYL ESTERS

The invention is an improved method for making methyl-6-methoxy-1-naphthalenecarboxylate. This compound is a useful intermediate in the synthesis of tolrestat, as described in J. Med. Chem., Vol. 27, 255 (1984).

This methyl ester was previously made by fusion of anisole and 2-furoic acid followed by esterification of the acid intermediate, J. Amer. Chem. Soc., Vol. 69, 2261 (1947). Methyl esters of methoxy carboxylic acids were prepared by methylation of aromatic hydroxy carboxylic acids with dimethyl sulfate in the presence of potassium carbonate as base, using acetone as the solvent, Houben-Weyl, Methoden der Organischen Chemie., Vol. 8, 542–3 (1952). Methylation of 2-hydroxy-1-naphthoic acid with dimethyl sulfate in aqueous sodium or potassium hydroxide produced mainly methyl-2-methoxy-1-naphthalenecarboxylate, Chemische Berichte, Vol. 37, 3658–61 (1904). In aqueous solutions, at pH 4–6.5, methylation of hydroxy napthoic acids with dimethyl sulfate produced the methyl esters of the hydroxy naphthoic acids.

An object of the invention is to methylate 6-hydroxy-1-naphthoic acid with dimethyl sulfate in a water insoluble organic solvent to produce suitably high yields of methyl-6-methoxy-1-naphthalene carboxylate:

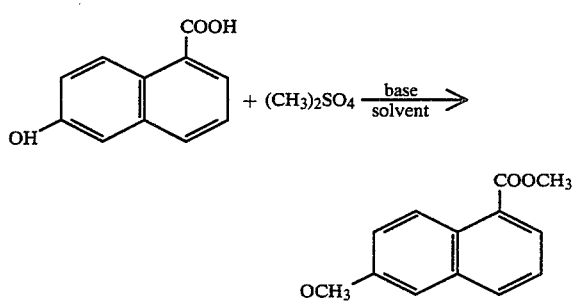

Use of acetone as solvent, as in the Houben-Weyl process mentioned above was deemed undesirable due to the flammability and low flash point ($-18°$ C.) of acetone. Use of a low molecular weight aliphatic ester such as butyl acetate was particularly preferred because such solvents would have higher flash points (butyl acetate, 22° C.) and because their insolubility in water is amenable to a simple method for product separation. It was found, however, that the methylation with dimethyl sulfate in butyl acetate in presence of either potassium hydroxide or potassium carbonate would produce only low yields of the dimethylated product. It was unexpected to discover that product yields were very much improved by the use of a combination of potassium carbonate and potassium hydroxide.

Preferred solvents for carrying out the invention are liquid organic solvents having a flash point (closed cup) of greater than 10° C., and which are insoluble in water. Such solvents include aliphatic esters such as n-propyl acetate, n-butyl acetate, isobutyl acetate, n-amyl acetate, isoamyl acetate, hexyl acetate, ethyl propionate, isoamyl propionate, methyl butyrate, ethyl butyrate and amyl butyrate.

As the base in a reaction carried out according to the invention one will use a combination of alkali metal carbonates and hydroxides, particularly carbonates and hydroxides of potassium and sodium. The ratio of alkali carbonate to alkali hydroxide in the reaction mixture will usually be in the range from 1:1 to about 20:1 on a molar basis. We prefer to use a large molar excess of the carbonate, e.g. about 10 or more moles carbonate per mole hydroxide.

EXAMPLE 1

6-Hydroxy-1-naphthalenecarboxylic acid, 31.7 g (0.17 mole), is dissolved into 200 mL of butyl acetate with stirring and heating to 75° C. Added all at once is powdered potassium carbonate, 24.5 g (0.175 mole). Dimethyl sulfate, 25.2 g (0.2 mole), is then added dropwise over five minutes. The mixture is stirred at 85°–90° C. for one hour, cooled to 65° C., and an additional powdered potassium carbonate, 24.5 g (0.175 mole), is added. Also 1:1 g (0.02 mole), of potassium hydroxide as a 22 wt. % aqueous solution is added dropwise over 1–2 minutes. Then additional dimethyl sulfate, 25.3 g (0.20 mole), was added dropwise over one-half hour at 65°–80° C. At this point a thin layer chromatographic analysis (TLC) of the reaction mixture indicates the desired product, methyl 6-methoxy-1-naphthalenecarboxylate, present. Starting material and methyl 6-hydroxy-1-naphthalenecarboxylate are not observed. The reaction mixture is heated at 70°–75° C. with stirring for an additional hour with no change in the TLC. A total of 11.5 mole % excess base and 19.3 mole % excess dimethyl sulfate has been charged.

Product methyl 6-methoxy-1-naphthalenecarboxylate is isolated according to the method in Example 5 to give 30.9 g, (assay 93.0%); 78% yield was obtained.

EXAMPLE 2

6-Hydroxy-1-naphthalenecarboxylic acid, 31.7 g (0.17 mole), is dissolved into 400 mL of butyl acetate with stirring and heating to 75°–80° C. Added all at once is 24.5 g (0.175 mole) powdered potassium carbonate. Dimethyl sulfate, 25.4 g (0.2 mole), is added dropwise over 15 minutes. The mixture is stirred at 85°–90° C. for two hours. Added is additional powdered potassium carbonate, 24.5 g (0.175 mole) and additional dimethyl sulfate, 25.4 g (0.2 mole), dropwise over five minutes. Stirring of the mixture is continued with heating at 85°–90° C. for one hour. A TLC of the mixture shows no starting material and about equal amounts of intermediate methy 1 6-hydroxy-1-napthalenecarboxylate and product methyl 6-methoxy-1-naphthalene carboxylate. After another one-half hour of heating at 85°–90° C., the mixture TLC has not changed. Added dropwise over one-two minutes is 1.1 g (0.02 mole) of potassium hydroxide as a 22 wt. % aqueous solution. The mixture is heated at 85°–91° C. with stirring for one hour. TLC shows mostly desired product, and practically no intermediate. The mixture is heated at 85°–90° C. for one hour. No further change is observed by TLC. A total of 11.5 mole % excess base and 20 mole % excess dimethyl sulfate has been charged.

Product methyl 6-methoxy-1-naphthalenecarboxylate is isolated according to the method in Example 5, and 30.8 g (assay 89.7%), 76% yield is obtained.

EXAMPLE 3

6-Hydroxy-1-naphthalenecarboxylic acid, 31.7 g, is dissolved into 250 mL of butyl acetate with stirring and heated to 45° C. Added over 10 minutes at 45°–50° C. is

TABLE 1

$$\text{HO-C}_{10}\text{H}_5\text{-CO}_2\text{H} + (CH_3)_2SO_4 \longrightarrow CH_3O\text{-C}_{10}\text{H}_5\text{-CO}_2CH_3$$

|  | EX. 1 | EX. 2 | EX. 3 | EX. 4 | EX. 5 |
|---|---|---|---|---|---|
| 6-Hydroxy-1-Naphthoic Acid (mole) | 0.17 | 0.17 | 0.17 | 0.17 | 0.17 |
| Dimethyl Sulfate (mole) | 0.40 | 0.40 | 0.47 | 0.34 | 0.60 |
| KOH (mole) | 0.02 | 0.02 | 0.36 | 0 | 0 |
| $K_2CO_3$ (mole) | 0.35 | 0.35 | 0 | 0.35 | 0.84 |
| n-Butyl Acetate (ml) | 200 | 400 | 250 | 500 | 450 |
| Reaction Temperature (°C.) | 65–90 | 85–90 | 50–75 | 50–93 | 85–90 |
| Percent Yield of 6-Methoxy-1-Naphthoic Acid, Methyl Ester | 78.4 | 76.0 | 36.8 | 16.7 | 28.6 |

I claim:

1. In the synthesis of methyl 6-methoxy-1-naphthalene carboxylate by methylation of 6-hydroxy-1-naphthoic acid with dimethyl sulfate in a liquid organic solvent and in presence of a base, the improvement wherein the liquid organic solvent has a flash point (closed cup) greater than 10° C. and is insoluble in water, and the base is a combination of a alkali metal carbonate and alkali metal hydroxide.

2. A method defined by claim 1 wherein the liquid organic solvent is an aliphatic ester.

3. A method defined by claim 2 wherein the base is a combination of potassium carbonate and potassium hydroxide.

4. A method defined by claim 3 wherein the aliphatic ester solvent is butyl acetate.

5. A method defined by claim 1 wherein the mole ratio of alkali metal carbonate to alkali metal hydroxide used in combination as the base is in the range from 1:1 to about 20:1.

6. A method defined by claim 5 wherein the base is a combination of potassium carbonate and potassium hydroxide.

7. A method defined by claim 6 wherein the liquid organic solvent is butyl acetate.

8. A method defined by claim 2 wherein the mole ratio of alkali metal carbonate to alkali metal hydroxide is at least 10:1.

* * * * *